(12) United States Patent
Russomanno et al.

(10) Patent No.: US 12,274,561 B2
(45) Date of Patent: *Apr. 15, 2025

(54) MULTI-PURPOSE EAR APPARATUS FOR MEASURING ELECTRICAL SIGNAL FROM AN EAR

(71) Applicant: OpenBCI, Inc., Brooklyn, NY (US)

(72) Inventors: Conor Russomanno, Brooklyn, NY (US); Shi Gang Yuan, Middle Island, NY (US); Joseph Artuso, Brooklyn, NY (US); Musa Mahmood, Brooklyn, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/392,930

(22) Filed: Dec. 21, 2023

(65) Prior Publication Data

US 2024/0122538 A1   Apr. 18, 2024

Related U.S. Application Data

(63) Continuation of application No. 18/324,547, filed on May 26, 2023, now Pat. No. 11,850,067.

(Continued)

(51) Int. Cl.
*A61B 5/01* (2006.01)
*A61B 5/00* (2006.01)
(Continued)

(52) U.S. Cl.
CPC .......... *A61B 5/6803* (2013.01); *A61B 5/6817* (2013.01); *G06F 1/163* (2013.01); *A61B 5/02055* (2013.01)

(58) Field of Classification Search
CPC ............ A61B 5/02055; A61B 5/02416; A61B 5/02417; A61B 5/02438; A61B 5/291; A61B 5/296; A61B 5/318; A61B 5/6803; A61B 5/6815; A61B 5/6817; A61B 5/6826; A61B 5/0006; A61B 5/01; A61B 5/021; A61B 5/02427; A61B 5/1075; A61B 5/4836; A61B 5/4848; A61B 5/6819; A61B 5/721; A61B 5/7445; A61F 11/08; G06F 1/163; G06F 1/203; G06F 3/015; H04R 1/105; H04R 25/305; H04R 25/609;

(Continued)

(56) References Cited

U.S. PATENT DOCUMENTS 6,647,368 B2 * 11/2003 Nemirovski ............. H04R 3/02
704/271
7,639,824 B2 * 12/2009 Franzen ................. H04R 5/033
381/151

(Continued)

*Primary Examiner* — Gerald Gauthier
(74) *Attorney, Agent, or Firm* — Esplin & Associates, PC (57) ABSTRACT

An ear apparatus may comprise one or more of a housing, an electrode, a biometric sensor, a speaker driver, and/or other components. The housing of the ear apparatus may be configured to be attached to an ear. The electrode may be carried by the housing. The electrode may be configured to measure an electrical signal from the ear. The electrical signal may include a reference signal, a ground signal, or a bias signal. The biometric sensor may be carried by the housing. The biometric sensor may be configured to measure one or more biometric characteristics from the ear. The speaker driver may be carried by the housing. The speaker driver may be configured to produce sound.

28 Claims, 6 Drawing Sheets

600

Measure an electrical signal from an ear via an electrode carried by an ear apparatus, the electrical signal including a reference signal or a ground signal
602

Measure one or more biometric characteristics from the ear via a biometric sensor carried by the ear apparatus
604

Produce sound via a speaker driver carried by the ear apparatus
606

Related U.S. Application Data (60) Provisional application No. 63/346,348, filed on May 27, 2022.

(51) Int. Cl.
*G06F 1/16* (2006.01)
*A61B 5/0205* (2006.01)

(58) Field of Classification Search
CPC ...... H04R 25/658; H04R 1/10; H04R 1/1016; H04R 1/1091; H04R 1/245; H04R 1/2857; H04R 3/02; H04R 5/033; H04R 25/02; H04R 25/60; H04R 29/001; G02B 6/4246; H01R 11/30
See application file for complete search history.

(56) References Cited

U.S. PATENT DOCUMENTS

| | | | | |
|---|---|---|---|---|
| 8,014,553 | B2* | 9/2011 | Radivojevic | H04R 25/305 381/151 |
| 8,577,427 | B2* | 11/2013 | Serota | H04R 1/105 379/430 |
| 8,958,589 | B2* | 2/2015 | Llic | H04R 25/60 381/381 |
| 9,497,534 | B2* | 11/2016 | Prest | H04R 1/1091 |
| 9,705,605 | B2* | 7/2017 | Masarik | G02B 6/4246 |
| 9,750,462 | B2* | 9/2017 | LeBoeuf | A61B 5/4848 |
| 9,858,030 | B2* | 1/2018 | Serota | G06F 1/203 |
| 10,617,297 | B2* | 4/2020 | Turner | A61B 5/0006 |
| 10,674,958 | B2* | 6/2020 | Bleich | A61B 5/021 |
| 11,311,228 | B1* | 4/2022 | Oakley | A61B 5/0006 |
| 11,523,202 | B2* | 12/2022 | Au | H04R 25/609 |
| 11,716,580 | B2* | 8/2023 | Solum | A61B 5/01 381/87 |
| 11,850,067 | B1* | 12/2023 | Russomanno | A61B 5/291 |
| 12,013,724 | B1* | 6/2024 | Russomanno | A61B 5/6815 |
| 2008/0199035 | A1* | 8/2008 | Flechel | H04R 1/1075 381/380 |
| 2008/0298623 | A1* | 12/2008 | Klein | H04R 1/2857 381/380 |
| 2010/0217100 | A1* | 8/2010 | LeBoeuf | A61B 5/6826 600/382 |
| 2010/0331631 | A1* | 12/2010 | MacLaughlin | A61B 5/7445 600/324 |
| 2012/0189155 | A1* | 7/2012 | Gabara | H01R 11/30 439/38 |
| 2013/0121518 | A1* | 5/2013 | Dahl | H04R 1/10 381/328 |
| 2013/0188819 | A1* | 7/2013 | Young-Mun | H04R 1/1016 181/129 |
| 2015/0382120 | A1* | 12/2015 | Baskaran | H04R 29/001 381/56 |
| 2017/0095202 | A1* | 4/2017 | Facteau | H04R 25/02 |
| 2017/0112408 | A1* | 4/2017 | Durand | A61B 5/4836 |
| 2018/0220911 | A1* | 8/2018 | Hiwaki | A61B 5/6819 |
| 2019/0098388 | A1* | 3/2019 | Powell | H04R 1/105 |
| 2019/0192077 | A1* | 6/2019 | Kaiser | G06F 3/015 |
| 2019/0216395 | A1* | 7/2019 | Geva | A61B 5/02438 |
| 2019/0223747 | A1* | 7/2019 | Chou | A61B 5/291 |
| 2019/0246982 | A1* | 8/2019 | Mackellar | A61B 5/291 |
| 2019/0306594 | A1* | 10/2019 | Aumer | H04R 1/1091 |
| 2019/0380597 | A1* | 12/2019 | Howard | A61B 5/318 |
| 2020/0092634 | A1* | 3/2020 | Wagner | A61B 5/721 |
| 2021/0022636 | A1* | 1/2021 | Zhu | A61B 5/02055 |
| 2021/0177352 | A1* | 6/2021 | Pintat | A61B 5/6817 |
| 2021/0243516 | A1* | 8/2021 | Tan | H04R 1/245 |
| 2022/0257186 | A1* | 8/2022 | Stewart | H04R 25/658 |
| 2022/0313099 | A1* | 10/2022 | Chang | A61B 5/6803 |
| 2022/0394396 | A1* | 12/2022 | Gallégo | A61B 5/296 |
| 2023/0156389 | A1* | 5/2023 | Keady | A61F 11/08 381/380 |
| 2024/0122538 | A1* | 4/2024 | Russomanno | A61B 5/6815 |

* cited by examiner

MULTI-PURPOSE EAR APPARATUS FOR MEASURING ELECTRICAL SIGNAL FROM AN EAR

CROSS-REFERENCE TO RELATED APPLICATIONS

The present application claims the benefit of U.S. Provisional Application No. 63/346,348, entitled "SYSTEM, METHOD, COMPONENT, AND INTERFACE OF HEAD-MOUNTED DISPLAY (HMD)," which was filed on: May 27, 2022, the entirety of which is hereby incorporated herein by reference.

FIELD

The present disclosure relates generally to the field of measuring an electrical signal from an ear using an ear apparatus.

BACKGROUND

Sensors that acquire biometric data from a person's head may require an electrical reference that is not affected by different electrical signals coming from the head. The electrical reference may be acquired from a part of the person that does not have brain or muscle activity, such as the person's ear(s). However, placing sensor(s) on the person's ear(s) may prohibit the person from using headphones.

SUMMARY

This disclosure relates to an ear apparatus. The ear apparatus may comprise one or more of a housing, an electrode, a biometric sensor, a speaker driver, and/or other components. The housing of the ear apparatus may be configured to be attached to an ear. The electrode may be carried by the housing. The electrode may be configured to measure an electrical signal from the ear. The electrical signal may include a reference signal or a ground signal. The biometric sensor may be carried by the housing. The biometric sensor may be configured to measure one or more biometric characteristics from the ear. The speaker driver may be carried by the housing. The speaker driver may be configured to produce sound.

In some implementations, the biometric sensor may include a photoplethysmography sensor.

In some implementations, the housing may include a flexible portion made of conductive polymer. The flexible portion of the housing may be configured to contact back, earlobe, and/or mastoid of the ear when the housing is attached to the ear. The electrical signal may be measured from the back, the earlobe, and/or the mastoid of the ear. In some implementations, the flexible portion of the housing may be curved and elongated.

In some implementations, the flexible portion of the housing may be the electrode configured to measure the electrical signal from the ear. In some implementations, the electrode configured to measure the electrical signal from the ear may be inside the flexible portion of the housing.

In some implementations, the ear apparatus may further comprise an electrical connector. The electrical connector may be carried by the housing. The electrical connector may include a first contact for the reference signal, a second contact for an audio signal, and a third contact for the ground signal, and/or a fourth contact for a bias signal.

In some implementations, the housing may include a first body piece and a second body piece. The first body piece and the second body piece may be connected via a hinge. The electrode may be carried by the first body piece, and the biometric sensor may be carried by the second body piece. The electrode may be further configured to inject a bias signal into the ear. The electrode carried by the first body piece of the housing may be configured to contact a first side of an earlobe when the housing is attached to the ear. The biometric sensor carried by the second body piece of the housing may be configured to contact a second side of the earlobe when the housing is attached to the ear.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

DETAILED DESCRIPTION

The present disclosure relates to an ear apparatus. The ear apparatus may comprise one or more of a housing, an electrode, a biometric sensor, a speaker driver, and/or other components. The housing of the ear apparatus may be configured to be attached to an ear. The electrode may be carried by the housing. The electrode may be configured to measure an electrical signal from the ear. The electrical signal may include a reference signal or a ground signal. The biometric sensor may be carried by the housing. The biometric sensor may be configured to measure one or more biometric characteristics from the ear. The speaker driver may be carried by the housing. The speaker driver may be configured to produce sound.

Augmented reality (AR)/virtual reality (VR) devices, such as headgear with head-mounted display, may require headphones (e.g., over-ear headphones, on-ear headphones, earbud headphones, in-ear headphones) to hear the sounds coming from the devices. Use of headphones may allow the users to hear the sounds with higher fidelity than when the sounds are produced through speakers embedded in the AR/VR devices. Sensors that acquire physiological data from a person's head may require an electrical reference that is not affected by different electrical signals coming from the head. The electrical reference may be acquired from a part of the person that does not have brain or muscle activity, such as the person's ear(s). The ear(s) may be far enough away from the brain or facial muscles to add noise to the system.

This poses a problem as placement of sensor(s) on the person's ear(s) may prohibit the person from using headphones, such as over-ear headphones. Additionally, headphones may introduce an audio signal in/near the ear(s), which may negatively impact the quality of the reference signal measured from the ear(s).

The present disclosure provides a multi-purpose ear apparatus to overcome the above and other deficiencies. The multi-purpose ear apparatus provides multiple functionalities, such as measuring electrical signals (e.g., reference signal, ground signal) from the ear, producing sound(s), and/or measuring biometric characteristic(s) of the person from the ear(s). The multi-purpose ear apparatus may combine the audio, electrical, and/or biometric connections into a single device. To eliminate/reduce the noise coming from audio signals, the wires of the multi-purpose ear apparatus may be shielded.

Figure 1:
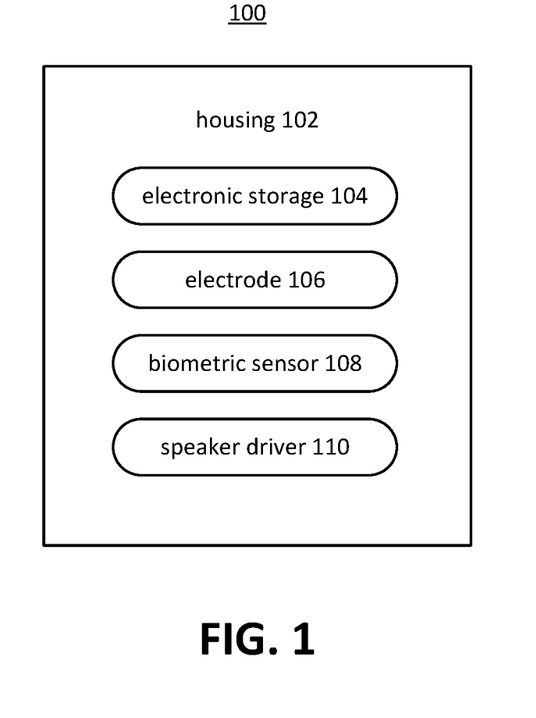
FIG. 1 illustrates an example ear apparatus.

FIG. 1 illustrates an example ear apparatus 100. The ear apparatus 100 may comprise one or more of a housing 102, an electronic storage 104, an electrode 106, a biometric sensor 108, a speaker driver 110, and/or other components. The housing 102 may refer to a device (e.g., casing, shell) that covers, protects, and/or supports one or more components of the ear apparatus 100. The housing 102 may include a single-piece housing or a multi-piece housing. References to the housing of an ear apparatus may refer to the ear apparatus, and vice versa.

The housing 102 of the ear apparatus 100 may be configured to be attached to an ear. The housing 102 being configured to be attached to an ear may include the housing 102 having physical attributes/characteristics that enables the housing to be attached to (e.g., worn on, carried by, affixed to, clipped to, hang from) the ear. For example, one or more parts of the housing 102 may be shaped to be attached to the ear or inserted into the ear canal.

The housing 102 may carry one or more components of the ear apparatus 100. The housing 102 may carry (be attached to, support, hold, and/or otherwise carry) one or more of the electronic storage 104, the electrode 106, the biometric sensor 108, the speaker driver 110, and/or other components. In some implementations, the housing 102 may carry multiple electronic storage, multiple electrodes, multiple biometric sensors, multiple speaker drivers, and/or multiples of other components. Other configurations of ear apparatus are contemplated.

The electronic storage 104 may be configured to include an electronic storage medium that electronically stores information. The electronic storage 104 may store software algorithms, information determined by one or more processors, information received remotely, and/or other information that enables the ear apparatus 100 to function properly. For example, the electronic storage 104 may store information relating to the ear apparatus 100, information relating to components of the ear apparatus 100, information relating to reference signal, information relating to ground signal, information relating to bias signal, information relating to biometric characteristics, information relating to sound, and/or other information.

The electrode 106 may refer to an electric conductor. The electrode 106 may refer to a conductor through which electricity may enter or leave. The electrode 106 may include electrically conductive material(s). The electrode 106 may be configured to measure one or more electrical signals from the ear. The electrode 106 measuring an electrical signal from the ear may include the electrode 106 acquiring, ascertaining, conducting, obtaining, receiving, transferring, and/or otherwise measuring the electrical signal from the ear. The electrode 106 may measure the electrical signal(s) for another device, such as the biometric sensor 108, other sensors, and/or processor(s). In some implementations, the electrode 106 may be part of another device, such as a sensor.

The electrode 106 may measure electrical signal(s) generated by the ear, electrical signal(s) traveling through the ear, and/or other electrical signal(s) in/on the ear. The electrical signal(s) may be generated from one or more parts of the body. The electrical signal(s) measured by the electrode 106 may include a reference signal, a ground signal, and/or other electrical signals.

The reference signal may refer to a standard signal against which other signals acquired from the body are compared. The reference signal may refer to a standard measurement from which measurements from biometric sensors (e.g., biometric sensors on the ear apparatus 100, biometric sensors on a headgear) are compared. The signals/measurements acquired from the body may be compared to the standard signal/measurement provided by the reference signal measured from the ear to produce outputs. For example, the reference signal measured from the ear (e.g., earlobe) may be used as a reference for electroencephalography measurements.

The ground signal may refer to a signal that provides the reference point/ground for electrical devices. The ground signal may refer to a signal that provides a reference point from which voltages are measured. The ground signal measured from the ear may be used as electrical ground for operations of the ear apparatus 100 and/or an electrical device (e.g., headgear) connected to the ear apparatus 100.

The electrode 106 may be configured to inject one or more electrical signals into the ear. The electrode 106 injecting an electrical signal into the ear may include the electrode 106 applying, driving, introducing, passing, transferring, and/or otherwise injecting the electrical signal into the ear. The electrode 106 may inject electrical signal(s) generated by another device, such as the ear apparatus 100 and/or an electrical device (e.g., headgear) connected to the ear apparatus 100.

For example, the electrode 106 may be configured to inject a bias signal into the ear. The bias signal may refer to a signal that counters noise in the body for biometric sensor measurements. For example, multiple types of biometric signals may be measured using multiple biometric sensors (e.g., biometric sensor(s) on the ear apparatus 100, biometric sensor(s) on electrical devices, such as a headgear, connected to the ear apparatus 100). The biometric signals measured by different biometric sensors may be compared to identify noise that is common to the biometric signals, such as common-mode interference. The common noise signal may be inverted (e.g., by the ear apparatus 100, by the headgear) to generate the bias signal. The bias signal may be injected into the ear to reduce/eliminate the noise (e.g., common-mode interference) in the body.

In some implementations, the same electrode may be used to measure different types of electrical signals from the ear. For example, the same electrode may be used to measure different biometric characteristics of a person from the person's ear at different times. In some implementations, different electrodes may be used to measure different types of electrical signals from the ear. For example, separate electrodes may be used to measure different biometric characteristics of a person from the person's ear(s) at the same time.

In some implementations, the same electrode may be used to measure electrical signals from the ear and to inject electrical signals into the ear. For example, the same electrode may be used to measure the ground signal from the ear at one or more moments in the time and to inject the bias signal into the ear at other moments in time. For instance, a signal multiplexer may be used to offer the flexibility of either connecting to ground or injecting the bias signal based on the amount of environmental noise.

In some implementations, different electrodes may be used to measure electrical signals from the ear and to inject electrical signals into the ear. For example, one electrode may be used to measure an electrical signal from the ear and another electrode may be used to inject the bias signal into the same or different ear. For instance, the reference signal may be measured from one ear while the bias signal may be injected into the other ear via two separate electrodes. The ground signal may be measured from one ear while the bias signal may be injected into the same ear via two separate electrodes.

The biometric sensor 108 may refer to a sensor that measures biometric data of a person, such as the biometric characteristics of the person. Biometric data of a person may refer to data/information relating to physical and/or behavioral characteristics of the person. Biometric data of a person may include physiological data of the person. Physiological data may refer to data/information about a person's bodily functions, such as heart rate, skin conductance, skin temperature, cortisol level, palmar sweat, and eye tracking. The biometric characteristics of a person may include physical and/or behavioral characteristics of the person. The biometric characteristics of a person may include physiological characteristics of the person. Other types of biometric data are contemplated. The biometric sensor 108 may include one or more sensors. The biometric sensor 108 may include multiple sensors of the same type. The biometric sensor 108 may include different sensors of different types.

The biometric sensor 108 may be configured to measure one or more biometric characteristics from the ear. The biometric sensor 108 measuring a biometric characteristic from the ear may include the biometric sensor 108 acquiring, ascertaining, conducting, obtaining, receiving, transferring, and/or otherwise measuring the biometric characteristic from the ear. The biometric sensor 108 may be configured to measure a biometric characteristic from the ear electrically, optically, and/or through other techniques. The biometric characteristic(s) may be measured from the ear and/or from materials on the ear. The biometric sensor 108 may output signals that convey, reflect, and/or otherwise indicate the measured biometric characteristic(s). The biometric sensor 108 may include one or more electrodes. In some implementations, the biometric sensor 108 may include a photoplethysmography (PPG) sensor, electroencephalography (EEG) sensor, electromyography (EMG) sensor, electrodermal activity (EDA) sensor, electrooculogram (EOG) sensor, functional near-infrared spectroscopy (fNIRS) sensor, motion sensor (e.g., accelerometer, inertial measurement unit, gyroscope), image sensor (e.g., camera), sound sensor (e.g., microphone), temperature sensor, and/or other sensors.

The speaker driver 110 may refer to an audio device for producing sound. The speaker driver 110 may refer to an audio device that converts electrical energy (e.g., audio signals) into mechanical wave energy (e.g., sound waves). The speaker driver 110 may include one or more transducers that produce sound. The speaker driver 110 may be a part of a speaker. The speaker driver 110 may be configured to produce sound. For example, the speaker driver 110 may be configured to convert audio signals into sound waves to produce sound. In some implementations, the audio signals may be obtained from a headgear with a head-mounted display. For example, a person may be wearing a headgear with a head-mounted display attachment to see AR/VR content. The AR/VR content may include audio content. The audio signals conveying the audio content may be converted by the speaker driver 110 into sound. Production of other sounds is contemplated.

Figure 2:
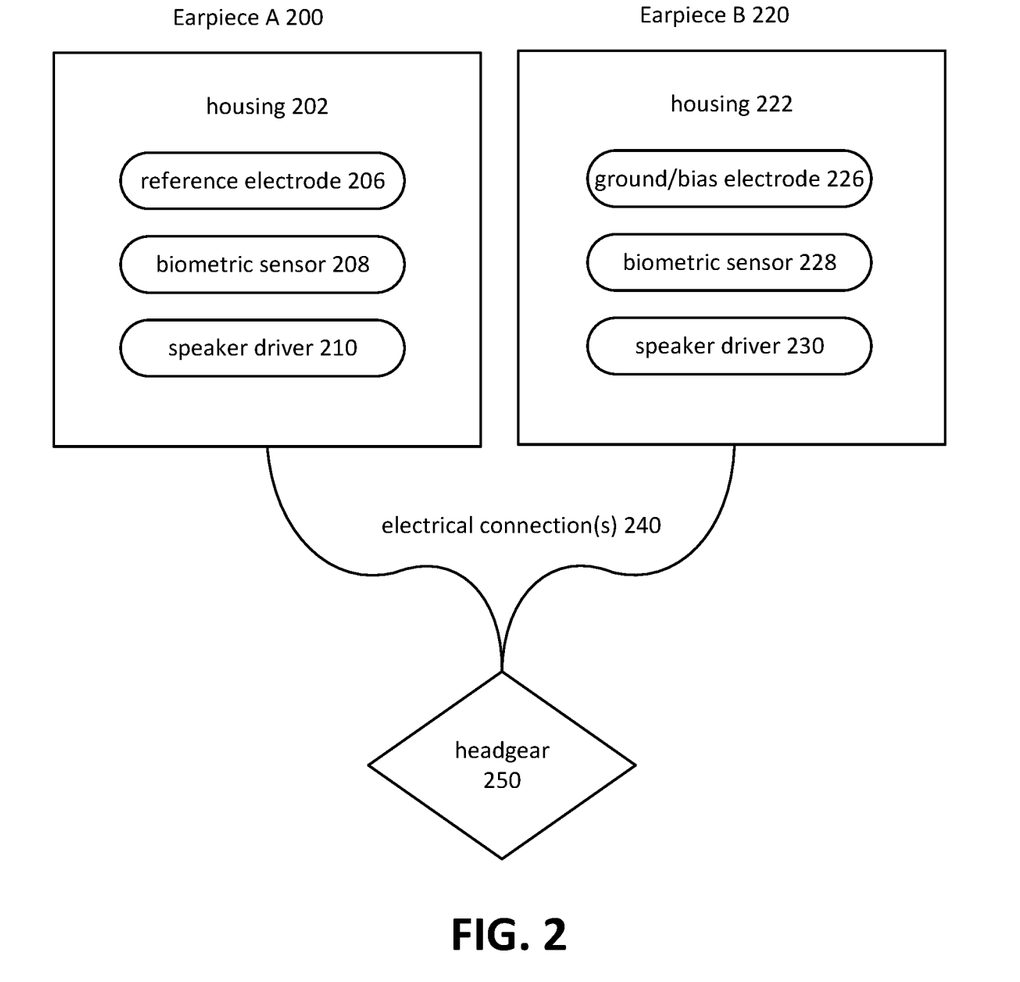
FIG. 2 illustrates an example ear apparatus.

FIG. 2 illustrates an example ear apparatus. The ear apparatus may include an earpiece A 200 and an earpiece 220 B. The earpiece A 200 and the earpiece 220 B may be configured (e.g., shaped) to be attached to different ears (left ear, right ear). The earpiece A 200 may include a housing 202, which may carry a reference electrode 206, a biometric sensor 208, a speaker driver 210, and/or other components. The reference electrode 206 may be configured to measure a reference signal from one ear. In some implementations, the reference signal may be measured continuously via the reference electrode 206. The biometric sensor 208 may be configured to measure biometric characteristic(s) from the ear. The speaker driver 210 may be configured to produce sound.

The earpiece B 220 may include a housing 222, which may carry a ground/bias electrode 226, a biometric sensor 228, an speaker driver 230, and/or other components. The ground/bias electrode 226 may be configured to measure a ground signal from the other ear. In some implementations, the ground signal may be measured periodically via the ground/bias electrode 226. The ground/bias electrode 206 may be configured to inject a bias signal into the other ear. The biometric sensor 228 may be configured to measure biometric characteristic(s) from the other ear. The speaker driver 230 may be configured to produce sound.

The earpiece A 200 and the earpiece 220 B may be connected to a headgear 250 via one or more electrical connections 240. The electrical connection(s) 240 may be shielded. The electrical connection(s) 240 may be contained within a wire harness. The earpiece A 200 and the earpiece 220 B may exchange information with the headgear 250 via the electrical connection(s) 240. For example, the earpiece A 200 may transmit information on the reference signal and/or biometric characteristic(s) measured by the earpiece A 200 to the headgear 250 via the electrical connection(s) 240. The earpiece B 200 may transmit information on the ground signal and/or biometric characteristic(s) measured by the earpiece B 220 to the headgear 250 via the electrical connection(s) 240. The headgear 250 may transmit information on sound to be produced by the speaker driver 210 to the earpiece A 220 via the electrical connection(s) 240. The headgear 250 may transmit information on sound to be produced by the speaker driver 230 to the earpiece B 220 via the electrical connection(s) 240. The headgear 250 may transmit information on the bias signal to be injected into the ear through the ground/bias electrode 226 to the earpiece B 220 via the electrical connection(s) 240. Exchange of other information is contemplated.

Figure 3:
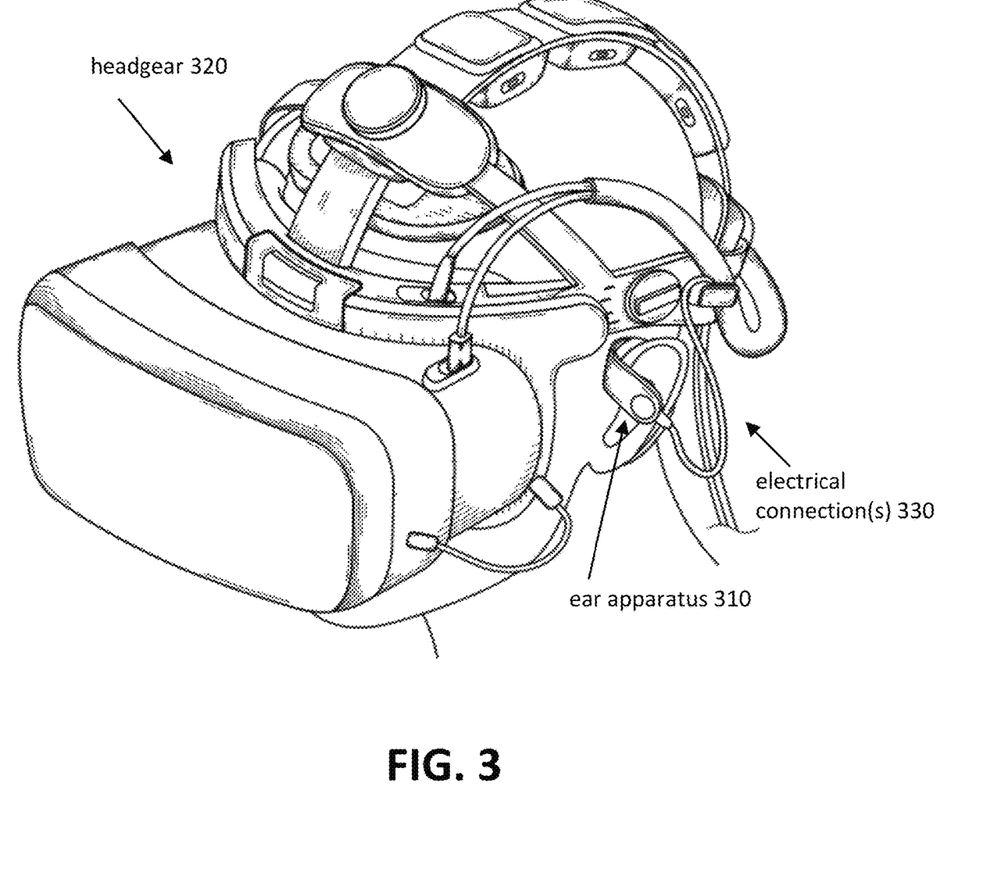
FIG. 3 illustrates an example ear apparatus connected to a headgear.

FIG. 3 illustrates an example ear apparatus 310 connected to a headgear 320. The ear apparatus 310 may include one or more of an electrode, a biometric sensor, a speaker driver, and/or other components. The ear apparatus 310 may be attached to an ear. For example, as shown in FIG. 3, the ear apparatus 310 may be attached to the left ear of a person. The electrode of the ear apparatus 310 may be configured to measure one or more electrical signals from the ear. The electrical signal(s) may include a reference signal, a ground signal, and/or other electrical signals. The electrode of the ear apparatus 310 may be configured to inject one or more electrical signals, such as a bias signal, into the ear. The biometric sensor of the ear apparatus 310 may be configured to measure one or more biometric characteristics from the ear. The speaker driver of the ear apparatus 310 may be configured to produce sound. The ear apparatus 310 may be connected to the headgear 320 through one or more electrical connections 330 (e.g., wire(s)). The electrical connection(s) 330 may be shielded. The electrical connection(s) 330 may be shielded to reduce/eliminate the noise in the information conveyed via the electrical connection(s).

The ear apparatus 310 may transmit information to the headgear 320 via the electrical connection(s) 330. For example, the ear apparatus 310 may transmit the electrical signal(s) measured via the electrode of the ear apparatus 310, the biometric characteristic(s) measured via the biometric sensor of the ear apparatus, and/or other information to the headgear 320 via the electrical connection(s) 330. The headgear 320 may transmit information to the ear apparatus 310 via the electrical connection(s) 330. For example, the headgear 320 may transmit information defining audio content, information defining bias signal to be injected into the ear, and/or other information to the ear apparatus 310 via the electrical connection(s) 330.

The ear apparatus 310 may facilitate functions/operations of the headgear 320. For example, information exchanged between the ear apparatus 310 and the headgear 320 via the electrical connection(s) 330 may facilitate functions/operations of the headgear 320. For instance, the headgear 320 may include a head-mounted display, one or more sensors, and/or other components. The head-mounted display of the headgear 320 may be configured to present visual content, such as AR content and/or VR content. The AR content and/or the VR content may include audio content (e.g., voice, music, song). The information defining the audio content may be transmitted from the headgear 320 to the ear apparatus 310 and the ear apparatus 310 may produce sound so that the person can hear the audio content from the ear apparatus 310 while watching the visual content on the head-mounted display.

The sensor(s) of the headgear 320 may be configured to acquire electrical signal(s) and/or optical signal(s) from the face to measure one or more biometric characteristics of the person. The electrical signal(s) (e.g., reference signal, ground signal) measured via the electrode of the ear apparatus 310 may be transmitted to the headgear 320 via the electrical connection(s) 330 for use in processing the biometric characteristic(s) measured by the sensor(s) of the headgear 320. The biometric signals measured via the sensor(s) of the headgear 320 may be compared to the reference signal measured by the ear apparatus 310 to produce outputs that indicate the biometric characteristics of the person. The ground signal measured by the ear apparatus 310 may be used as the electrical ground for the sensors/components of the headgear 320. Noise in the biometric signals measured by the sensor(s) of the headgear 320 may be inverted to generate a bias signal, and the bias signal may be injected into the ear by the ear apparatus 310 to reduce/eliminate noise (e.g., common-mode interference) from the acquisition of biometric signals. The ear apparatus 310 may facilitate other functions/operations of the headgear 320.

Referring back to FIG. 1, in some implementations, the housing 102 may include one or more flexible portions. The shape of a flexible portion of the housing 102 may be changed without breaking. For example, a flexible portion of the housing 102 may be bent without breaking. The shape of the flexible portion(s) of the housing 102 may be changed to fit the ear on which the housing 102 is attached to the ear, such as being carried by or worn on the ear. In some implementations, the flexible portion(s) of the housing may be curved and elongated. Use of other shapes is contemplated.

Some or all of the flexible portion(s) of the housing 102 may be made of conductive polymer. Conductive polymer may refer to one or more materials that conduct electricity. Conductive polymer may allow electrical signals to travel from the ear for measurement. In some implementations, the conductive polymer may be coated with one or more materials (e.g., silver/silver-chloride) to reduce electrical impedance. For example, conductive polymer may be made of a flexible, conductive material, such as silver powder in a silicone matrix, or graphite in a 3D printed UV resin. Conductive polymer may be treated with additional conductive coatings, such as silver/silver-chloride, to further increase its signal quality by reducing the electrical impedance between the polymer and the skin. Use of other types of conductive polymer/material is contemplated.

The flexible portion(s) of the housing 102 may be configured to contact the back, earlobe, mastoid, and/or part(s) of the ear when the housing 102 is attached to the ear. The electrical signal may be measured by the electrode 106 from the back, the earlobe, the mastoid, and/or other part(s) of the ear. The electrical signal may travel from the ear and through the conductive polymer of the flexible portion(s) of the housing 102 for measurement.

In some implementations, the flexible portion(s) of the housing 102 may be the electrode 106 configured to measure the electrical signal from the ear. That is, the electrode 106 that measures the electrical signal from the ear may be the flexible portion(s) of the housing 102. The conductive polymer of the flexible portion(s) may be used to measure the electrical signal from the ear. In some implementations, the electrode 106 configured to measure the electrical signal from the ear may be inside the flexible portion(s) of the housing. That is, the electrode 106 may be surrounded by, buried within, or otherwise contacting the conductive polymer of the flexible portion(s) and may measure the electrical signal that travels to the electrode 106 via the conductive polymer of the flexible portion(s).

In some implementations, the ear apparatus 100 may further comprise one or more electrical connectors. An electrical connector may refer to an electromechanical device used to create an electrical connection between different electrical devices. An electrical connector may be used to create an electrical connection between the ear apparatus 100 and one or more other electrical devices, such as a headgear as shown in FIG. 3. In some implementations, the electrical connector(s) may be shaped like an electrical plug used for audio and/or visual information exchange, such as a 3.5 mm TRS audio jack. Use of other shapes is contemplated.

The electrical connector(s) may be carried by the housing 102. The electrical connector(s) may include one or more contacts for one or more signals. For example, the electrical connector(s) may include a first contact for a reference signal, a second contact for an audio signal, a third contact for a ground signal, a fourth contact for a bias signal, and/or other contacts. The contact(s) may be used to transfer information (e.g., electrical signals, audio signals, information conveying biometric characteristics) between the ear apparatus 100 and the electrical device(s) to which the ear apparatus 100 is connected via the electrical connector(s). For example, multiple contacts of an electrical connector may be used to transfer audio signal information (e.g., left and/or right channel audio), reference signal information, ground signal information, bias signal information, and/or other information.

In some implementations, the same contact may be used to transfer different types of information. For example, the same contact may be used to transfer information defining reference signal, ground signal, audio signal, bias signal, and/or biometric characteristics, at different times. In some implementations, different contacts may be used to transfer different types of information. For example, separate contacts may be used to transfer information defining reference signal, ground signal, audio signal, bias signal, and/or biometric characteristics at the same time.

In some implementations, the audio component(s) and sensor component(s) of the ear apparatus 100 may be separated. For example, rather than carrying the speaker driver 110, the housing 102 may carry a female audio port via which an audio device may be electrically connected. The housing 102 may include one or more portions to which the audio device may be physically connected. For example, flexible portion(s) of the housing 102 may be configured to be wrapped around an earbud to mechanically hold it in place, and the earbud may be electrically plugged into the housing 102 via the female audio port.

Figure 4:
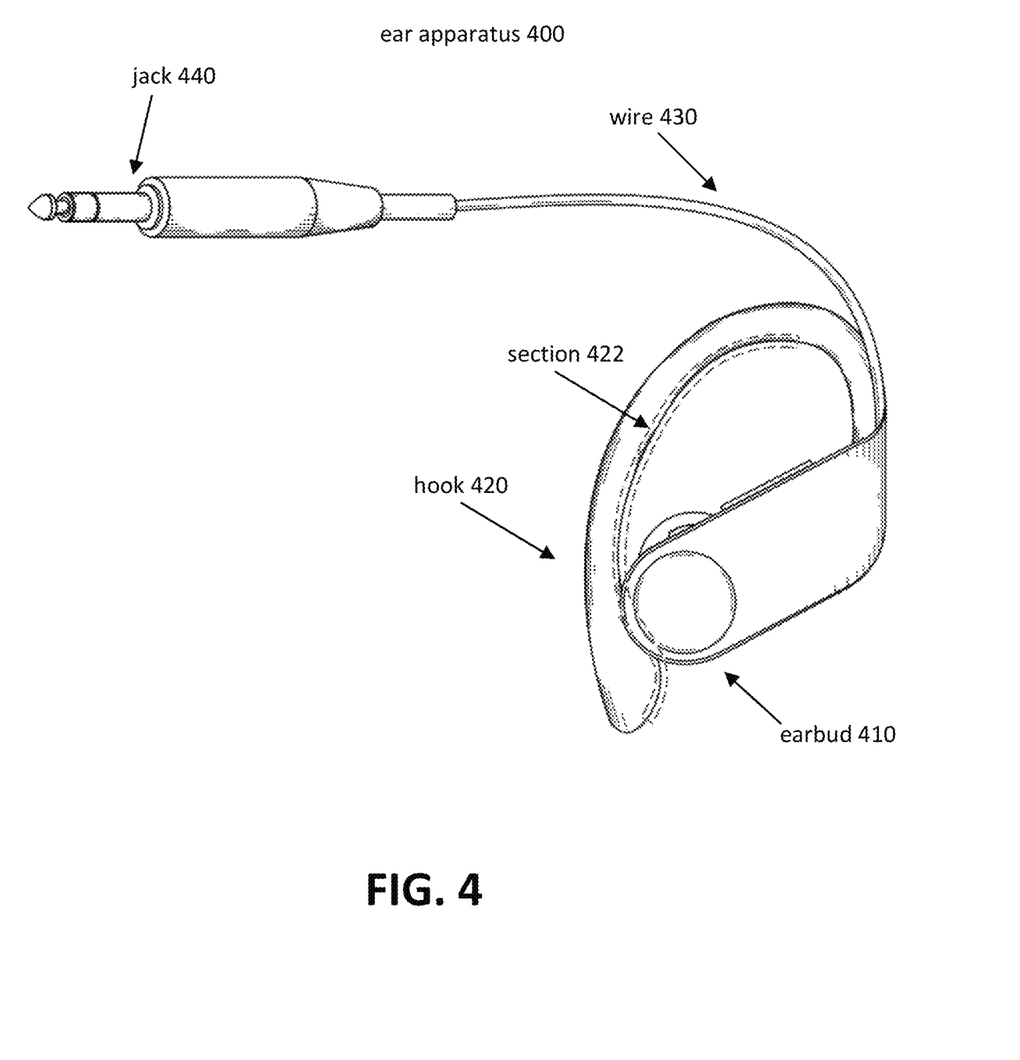
FIG. 4 illustrates an example flexible ear apparatus.

FIG. 4 illustrates an example flexible ear apparatus 400. The ear apparatus 400 may include an earbud 410, a hook 420, a wire 430, and a jack 440. The hook 420 may be flexible. The hook 420 may be placed around a person's ear to position the earbud 410 in the person's ear. When the hook 420 is placed around the person's ear, a section 422 of the hook 420 may contact the ear to create a reference.

The hook 420 may include conductive polymer. For example, one or more portions of the hook 420 may be over molded with a flexible conductive polymer. For instance, the section 422 of the hook 420 may include conductive polymer. The section 422 of the hook 420 may be an electrode or may include an electrode within. An electrical signal (e.g., reference signal, ground signal) may be measured via the contact of the section 422 with the back, the earlobe, and/or the mastoid of the ear.

The jack 440 may be used to electrically connect the ear apparatus 400 with another electrical device. For example, the jack 440 may be used to electrically connect the ear apparatus 400 with a headgear. Information may be exchanged between the ear apparatus and the electrical device via the jack 440. For example, the jack 440 may include a contact for audio signal, and audio signal may be transmitted from the headgear to the ear apparatus 400 for playback via the jack 440. The jack 440 may include one or more contacts for a reference signal, a ground signal, and/or other signals measured via the section 422 of the hook 420, and the signal(s) measured by via the section 422 may be transmitted from the ear apparatus 400 to the headgear for processing via the jack 440. The jack 440 may include a contact for a bias signal to be injected into the ear by the ear apparatus 400. The jack 440 may include other contacts, such as for system ground or shield.

While the ear apparatus is shown with a single jack in FIG. 4, this is merely as an example and is not meant to be limiting. The ear apparatus may include one or more wires, one or more jacks, one or more plugs (e.g., male plug(s) and/or female plug(s)), and/or other electrical connector(s) to enable exchange of information between the ear apparatus and other electrical device(s).

Referring back to FIG. 1, in some implementations, the housing 102 may include multiple body pieces. For example, the housing 102 may include a first body piece, a second body piece, and/or other body pieces. The body pieces of the housing 102 (e.g., the first body piece and the second body piece) may be connected via one or more hinges. The hinge(s) may include spring(s) and/or other mechanisms to bias the connected body pieces into a particular configuration. For example, two body pieces may be connected via a spring loaded hinge, which may bias the two body pieces into a closed position.

One or more electrodes and/or one or more biometric sensors may be carried by one or more of the body pieces of the housing 102. The same type of electrode or same type of biometric sensor may be carried on multiple body pieces of the housing 102. Different types of electrode or different types of biometric sensor may be carried on multiple body pieces of the housing 102. For example, the electrode 106 may be carried by one body piece of the housing 102 and the biometric sensor 108 may be carried by another body piece of the housing 102. The electrode 106 carried by body piece of one body piece of the housing 102 may be configured to contact one side of an earlobe or another part of the ear when the housing 102 is attached to the ear. The biometric sensor 108 carried by another body piece of the housing 102 may be configured to contact another (e.g., opposite) side of the earlobe when the housing 102 is attached to the ear. When the housing 102 is attached to (e.g., clipped onto) the ear (e.g., the earlobe), the electrode 106 and the biometric sensor 108 may be positioned to make measurements from different sides of the ear (e.g., opposite sides of the earlobe). When the housing 102 is attached to (e.g., clipped onto) the ear (e.g., the earlobe), the electrode 106 may be positioned to inject an electrical signal (e.g., bias signal) into one side of the ear (e.g., one side of the earlobe) while the biometric sensor 108 may be positioned to make measurements from the other side of the ear (e.g., opposite side of the earlobe). The ear apparatus 100 with multiple body pieces may further comprise one or more electrical connectors, one or more wires (e.g., wire harness), and/or other components.

Figure 5:
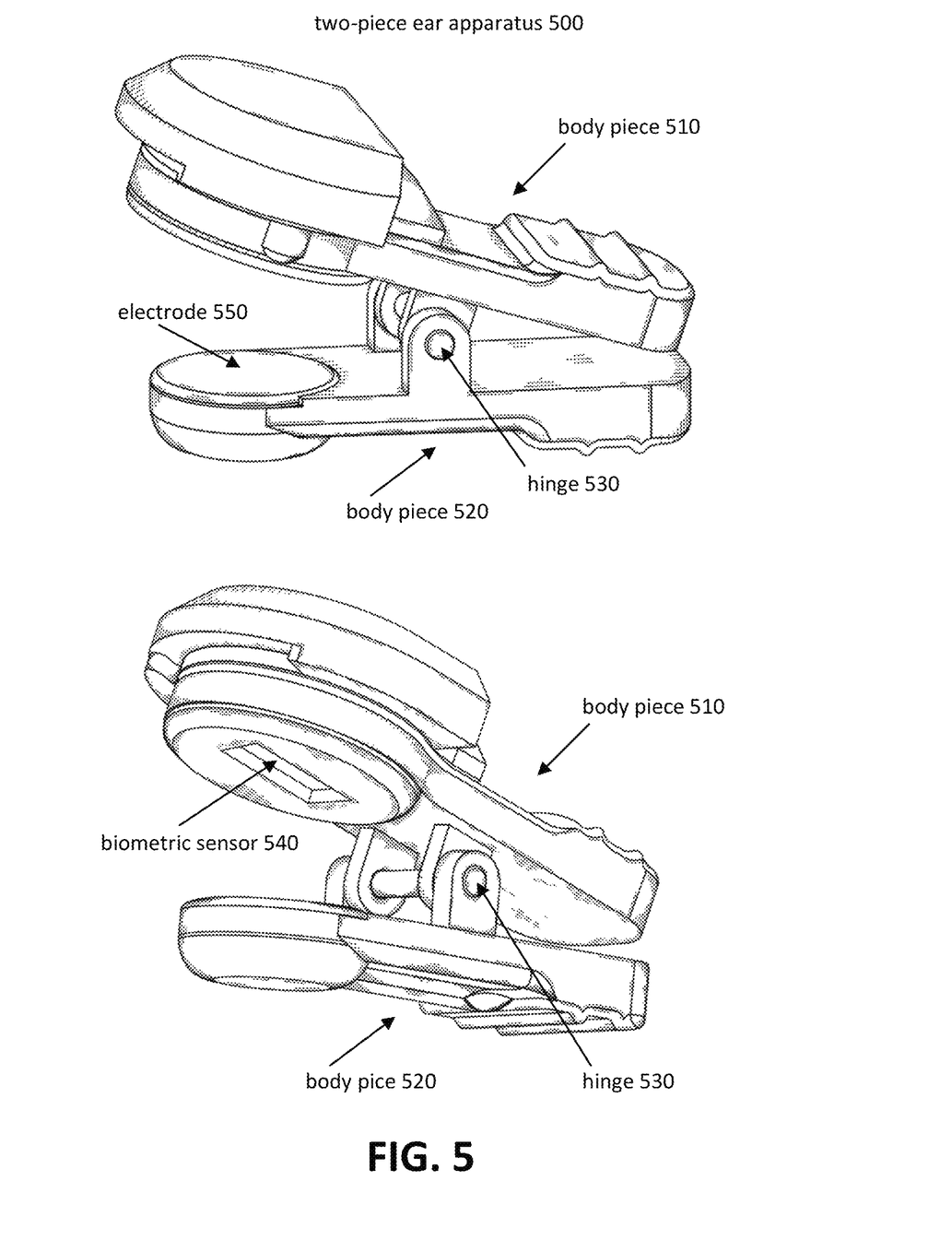
FIG. 5 illustrates an example two-piece ear apparatus.

FIG. 5 illustrates an example two-piece ear apparatus 500. The ear apparatus 500 may include a body piece 510 and a body piece 520, connected via a hinge 530. FIG. 5 may show views of the ear apparatus 500 in an open position. The body piece 510 and the body piece 520 may be biased into a closed position. The body piece 510 may include a biometric sensor 540, and the body piece 520 may include an electrode 550. When the ear apparatus 500 is attached to (e.g., clipped onto) the ear, the biometric sensor 540 and the electrode 550 may contact the ear to make measurements. When the ear apparatus 500 is attached to the ear, the electrode 550 may contact the ear to inject one or more electrical signals (e.g., bias signal) into the ear. Other configurations and placements of biometric sensors and electrodes are contemplated. The ear apparatus 500 may include components not shown in FIG. 5, such as one or more wires and/or one or more connectors, such as described with respect to the ear apparatus 400 shown in FIG. 4.

Figure 6:
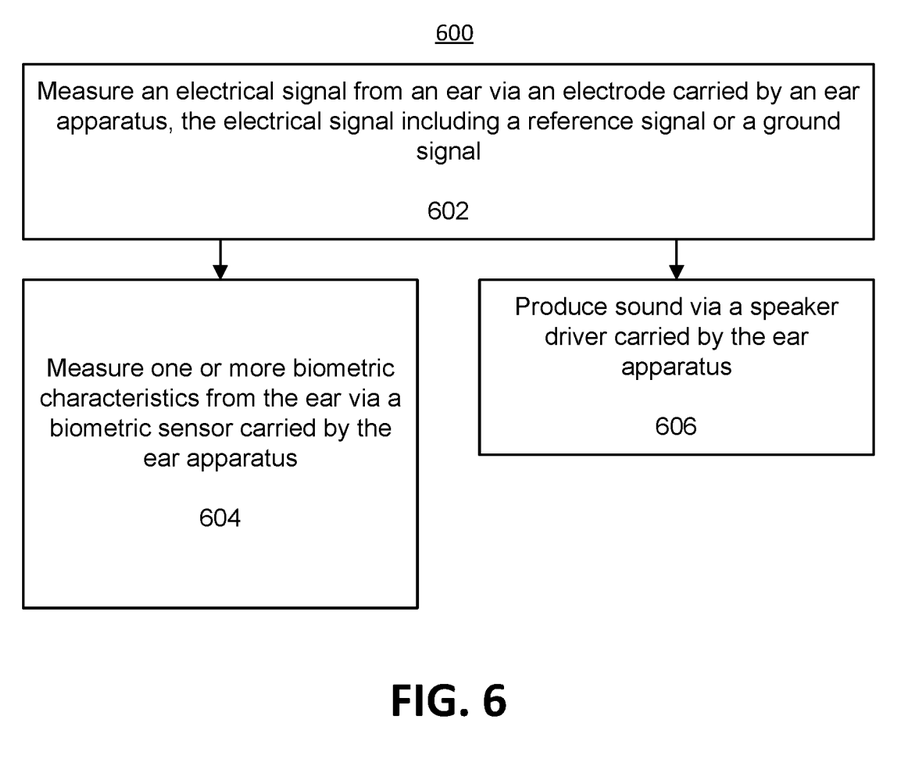
FIG. 6 illustrates an example method for utilizing an ear apparatus.

FIG. 6 illustrates method 600 for utilizing an ear apparatus. The operations of method 600 presented below are intended to be illustrative. In some implementations, method 600 may be accomplished with one or more additional operations not described, and/or without one or more of the operations discussed. In some implementations, two or more of the operations may occur substantially simultaneously.

At operation 602, an electrical signal may be measured from an ear via an electrode carried by an ear apparatus. The electrical signal may include a reference signal or a ground signal.

At operation 604, one or more biometric characteristics may be measured from the ear via a biometric sensor carried by the ear apparatus.

At operation 606, sound may be produced via a speaker driver carried by the ear apparatus.

Although the housing 102, the electronic storage 104, the electrode 106, the biometric sensor 108, and the speaker driver 110 are shown in FIG. 1 as single entities, this is for illustrative purposes only. One or more of the components of the ear apparatus 100 may be contained within a single device or across multiple devices. The components of the ear apparatus 100 may be physically and/or wirelessly connected. Any communication medium may be used to facilitate interaction between any components of the ear apparatus 100. One or more components of the ear apparatus 100 may communicate with each other through hard-wired communication, wireless communication, or both.

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. An ear apparatus system, comprising:
    a first earpiece configured to be attached to a first ear of a person, the first earpiece including a reference electrode configured to measure a reference signal from the first ear of the person; and
    a second earpiece configured to be attached to a second ear of the person, the second earpiece including a ground electrode configured to measure a ground signal from the second ear of the person or a bias electrode configured to inject a bias signal into the second ear of the person;
    wherein the first earpiece and the second earpiece are configured to be connected to a headgear, the headgear including one or more biometric sensors configured to measure one or more biometric signals from a head of the person, wherein connection between the headgear and the first and second earpieces enable the headgear to use the reference signal measured by the first earpiece from the first ear, use the ground signal measured by the second earpiece from the second ear, or inject the bias signal into the second ear of the person via the second earpiece.

2. The ear apparatus system of claim 1, wherein:
    the first earpiece includes a housing with a flexible portion made of conductive polymer, the flexible portion of the housing configured to contact the first ear of the person when the first earpiece is attached to the first ear;
    the flexible portion of the housing is configured to contact back, earlobe, and/or mastoid of the first ear when the housing is attached to the first ear; and
    the reference signal is measured from the back, the earlobe, and/or the mastoid of the first ear.

3. The ear apparatus system of claim 2, wherein the flexible portion of the housing is the reference electrode.

4. The ear apparatus system of claim 2, wherein the reference electrode is inside the flexible portion of the housing.

5. The ear apparatus system of claim 2, wherein the flexible portion of the housing is curved and elongated.

6. The ear apparatus system of claim 1, wherein the first earpiece further includes a first biometric sensor, and the reference signal measured by the first earpiece from the first ear is used as a reference for a first biometric characteristic measurement by the first biometric sensor of the first earpiece.

7. The ear apparatus of system claim 1, wherein the reference signal measured by the first earpiece from the first ear is used as a reference for one or more biometric characteristic measurements by the one or more biometric sensors of the headgear.

8. The ear apparatus of system claim 1, wherein the reference signal measured by the first earpiece from the first ear is used as a reference for an electroencephalography measurement.

9. The ear apparatus of system claim 1, wherein the ground signal measured by the second earpiece from the second ear is used as electrical ground for an operation of the second earpiece.

10. The ear apparatus system of claim 1, wherein the ground signal measured by the second earpiece from the second ear is used as electrical ground for an operation of the headgear connected to the second earpiece.

11. The ear apparatus system of claim 1, wherein the bias signal injected into the second ear of the person by the second earpiece reduces or eliminates noise in measurement of the one or more biometric signals from the head of the person by the one or more biometric sensors of the headgear.

12. The ear apparatus system of claim 1, wherein the first earpiece and/or the second earpiece further include a speaker driver configured to produce sound.

13. The ear apparatus system of claim 12, wherein the sound produced by the speaker driver includes audio content of augmented reality content or virtual reality content presented on a head-mounted display of the headgear.

14. The ear apparatus system of claim 1, wherein the first earpiece and/or the second earpiece includes a two-piece housing, the two piece housing including a first body piece and a second body piece connected via a hinge, the first body piece including a biometric sensor and the second body piece including an electrode, further wherein when the two-piece housing is attached to an ear, the biometric sensor and the electrode contacts opposite sides of the ear.

15. A method for utilizing an ear apparatus system, the method comprising:
    attaching a first earpiece to a first ear of a person, the first earpiece including a reference electrode configured to measure a reference signal from the first ear of the person; and
    attaching a second earpiece a second ear of the person, the second earpiece including a ground electrode configured to measure a ground signal from the second ear of the person or a bias electrode configured to inject a bias signal into the second ear of the person;
    wherein the first earpiece and the second earpiece are configured to be connected to a headgear, the headgear including one or more biometric sensors configured to measure one or more biometric signals from a head of the person, wherein connection between the headgear and the first and second earpieces enable the headgear to use the reference signal measured by the first earpiece from the first ear, use the ground signal measured by the second earpiece from the second ear, or inject the bias signal into the second ear of the person via the second earpiece.

16. The method of claim 15, wherein:
the first earpiece includes a housing with a flexible portion made of conductive polymer, the flexible portion of the housing configured to contact the first ear of the person when the first earpiece is attached to the first ear;
the flexible portion of the housing is configured to contact back, earlobe, and/or mastoid of the first ear when the housing is attached to the first ear; and
the reference signal is measured from the back, the earlobe, and/or the mastoid of the first ear.

17. The method of claim 16, wherein the flexible portion of the housing is the reference electrode.

18. The method of claim 16, wherein the reference electrode is inside the flexible portion of the housing.

19. The method of claim 16, wherein the flexible portion of the housing is curved and elongated.

20. The method of claim 15, wherein the first earpiece further includes a first biometric sensor, and the reference signal measured by the first earpiece from the first ear is used as a reference for a first biometric characteristic measurement by the first biometric sensor of the first earpiece.

21. The method of claim 15, wherein the reference signal measured by the first earpiece from the first ear is used as a reference for one or more biometric characteristic measurements by the one or more biometric sensors of the headgear.

22. The method of claim 15, wherein the reference signal measured by the first earpiece from the first ear is used as a reference for an electroencephalography measurement.

23. The method of claim 15, wherein the ground signal measured by the second earpiece from the second ear is used as electrical ground for an operation of the second earpiece.

24. The method of claim 15, wherein the ground signal measured by the second earpiece from the second ear is used as electrical ground for an operation of the headgear connected to the second earpiece.

25. The method of claim 15, wherein the bias signal injected into the second ear of the person by the second earpiece reduces or eliminates noise in measurement of the one or more biometric signals from the head of the person by the one or more biometric sensors of the headgear.

26. The method of claim 15, wherein the first earpiece and/or the second earpiece further include a speaker driver configured to produce sound.

27. The method of claim 26, wherein the sound produced by the speaker driver includes audio content of augmented reality content or virtual reality content presented on a head-mounted display of the headgear.

28. The method of claim 15, wherein the first earpiece and/or the second earpiece includes a two-piece housing, the two piece housing including a first body piece and a second body piece connected via a hinge, the first body piece including a biometric sensor and the second body piece including an electrode, further wherein when the two-piece housing is attached to an ear, the biometric sensor and the electrode contacts opposite sides of the ear.

* * * * *